(12) United States Patent (10) Patent No.: US 9,205,265 B2
Franke (45) Date of Patent: Dec. 8, 2015

(54) SYSTEMS AND METHODS FOR REMOVING CONTAMINATING NOISE FROM AN ELECTRIC WAVEFORM FOR NEURAL STIMULATION AND NERVE BLOCK

(71) Applicant: Case Western Reserve University, Cleveland, OH (US)

(72) Inventor: Manfred Franke, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/275,446

(22) Filed: May 12, 2014

(65) Prior Publication Data

US 2014/0336729 A1 Nov. 13, 2014

Related U.S. Application Data

(60) Provisional application No. 61/821,873, filed on May 10, 2013, provisional application No. 61/824,525, filed on May 17, 2013.

(51) Int. Cl.
*A61N 1/36* (2006.01)
*A61N 1/378* (2006.01)

(52) U.S. Cl.
CPC ........ *A61N 1/36142* (2013.01); *A61N 1/36125* (2013.01); *A61N 1/3782* (2013.01)

(58) Field of Classification Search
None
See application file for complete search history.

(56) References Cited

U.S. PATENT DOCUMENTS

| | | | | |
|---|---|---|---|---|
| 4,057,069 | A * | 11/1977 | Dorffer et al. | 607/61 |
| 6,293,266 | B1 * | 9/2001 | Oetting | 123/568.21 |
| 2011/0221438 | A1 * | 9/2011 | Goodwill et al. | 324/301 |
| 2014/0119480 | A1 * | 5/2014 | Keegan | 375/343 |

* cited by examiner

*Primary Examiner* — Erica Lee
(74) *Attorney, Agent, or Firm* — Tarolli, Sundheim, Covell & Tummino LLP

(57) ABSTRACT

One aspect of the present disclosure relates to a system that can remove contaminating noise (e.g., direct current (DC) contamination or high frequency contamination) from an electric waveform. The system can include a passive filter that includes at least a secondary-side-open-transformer-inductor (SOTI). The SOTI can include a first coil inductively coupled to a second coil. The first coil of the SOTI can receive the electric waveform contaminated with the noise and output the electric waveform. The second coil of the SOTI can provide an impedance that facilitates removal of the noise from the electric waveform.

19 Claims, 7 Drawing Sheets

SYSTEMS AND METHODS FOR REMOVING CONTAMINATING NOISE FROM AN ELECTRIC WAVEFORM FOR NEURAL STIMULATION AND NERVE BLOCK

RELATED APPLICATIONS

This application claims the benefit of U.S. Provisional Application No. 61/821,873, filed May 10, 2013, entitled "LC-BLOCKING-AND-DC-BALANCING CIRCUIT." This application also claims the benefit of U.S. Provisional Application No. 61/824,525, filed May 17, 2013, entitled "BALANCED ELECTRODE SYSTEM." The entirety of these provisional applications is hereby incorporated by reference for all purposes.

TECHNICAL FIELD

The present disclosure relates generally to neural stimulation and nerve block and, more specifically, to systems and methods that can remove contaminating noise from an electric waveform used for neural stimulation, nerve block, and/or neural sensing.

BACKGROUND

High-frequency alternating current waveforms in the kilohertz range (KHFAC) can provide a temporary nerve conduction block that does not provide a lasting effect on conduction. Similarly, direct current (DC) signals also can block conduction in the nerve. However, even at small amplitudes (e.g., a low micro Ampere (µA) range), after prolonged or repeated application, DC signals can damage the nerve tissue, leading to a lasting effect on conduction. For example, the lasting effect on conduction can be noticeable as a persistent reduction in nerve conductivity, even after the application of any kind of electric waveform has ended. This persistent reduction in nerve conductivity can be related to changes in pH levels at and/or within the nerve in close proximity to the electrode and can coincide with the damage of neural tissue.

Unintentional DC signals can contaminate KHFAC waveforms, leading to unexpected nerve block and/or damage. With lower frequency waveforms, techniques like additional capacitance and/or shunting resistance can be applied between the waveform generator and the electrode to substantially mitigate unintentional DC signals. However, these approaches are not feasible and/or not practical for use with higher frequency waveforms like KHFAC waveforms, especially current-controlled KHFAC waveforms. For example, the higher frequency waveforms do not allow the capacitors sufficient time to discharge the DC imbalance between stimulation pluses, so the unintentional DC signals that contaminate KHFAC waveforms cannot be substantially eliminated.

SUMMARY

The present disclosure relates generally to neural stimulation and nerve block and, more specifically, to systems and methods that can remove contaminating noise from an electric waveform used for neural stimulation, nerve block, and/or neural sensing. For example, electric waveforms used for neural stimulation and nerve block can have DC contamination that can damage the nerve. The systems and methods of the present disclosure can filter the DC contamination from the waveform used for neural stimulation or nerve block so that the waveform used for neural stimulation or nerve block does not unintentionally damage the nerve.

In one aspect, the present disclosure can include a system that removes noise from an electric waveform for neural stimulation or nerve block. The system can include a secondary-side-open-transformer-inductor (SOTI) that can provide a high impedance that facilitates the removal of the noise from the electric waveform. The SOTI can include a first coil and a second coil that are inductively coupled. A primary side of the SOTI can be configured to receive the electric waveform contaminated with the noise and output the electric waveform, and a secondary side of the SOTI can be configured to adjust the frequency-dependent impedance of the SOTI.

In another aspect, the present disclosure can include a method for eliminating noise from an electric waveform for neural stimulation or nerve block. The method can be performed by a passive filter system comprising a secondary-side-open-transformer-inductor (SOTI). The SOTI can provide a high impedance that facilitates the removal of the noise from the electric waveform by the filter system. The method can include the step of receiving the electric waveform contaminated with the noise. The electric waveform can be received by the SOTI. The method can also include the step of removing the noise from the electric waveform. The method can also include the step of outputting the electric waveform (with the contaminating noise removed).

In a further aspect, the present disclosure can include a device that removes contaminating noise from an electric signal for neural stimulation or nerve block. The device can include a passive filter system comprising a secondary-side-open-transformer-inductor (SOTI) and at least one passive component and/or at least one active component. The SOTI can include a first coil inductively coupled to a second coil. The SOTI can provide a high impedance that facilitates removal of the contaminating noise from the electric waveform.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "secondary-side-open-transformer-inductor (SOTI)" can refer to a device (e.g., a transformer or other device with multiple coupled coils) that can provide a frequency-dependent electric impedance for filters in neural stimulation and nerve block applications, as well as for filtering noise in applications in sensing neural or muscular signals (e.g., electroneurogram (ENG), electromyogram (EMG), electrooctogram (EOG), etc.). In some instances, a SOTI can include at least two electro-magnetically coupled coils (e.g., a primary coil and a secondary coil), each with two connectors. The two connectors of the primary coil can represent the input and output connection of the overall impedance of the device (in other words, the overall impedance is only measured between the two connectors of the primary coil). The two connectors of the secondary coil (or any additional coils on the non-primary side) can represent an, at least partially electrically open circuit of the device.

In some instances, the SOTI can be a transformer, with one primary and one secondary coil (each coil with only two contacts, or connectors) and with a high electro-magnetic coupling ratio between the two coils (e.g., 0.98), where the secondary coil is not connected to anything (e.g., the contacts of the secondary coil can be intentionally left open and insulated, each one by itself). Low frequency waveforms passing through the primary side will experience essentially only the impedance resulting from the wiring of the coil (e.g., direct current (DC) impedance). High frequency waveforms (e.g., 10 kHz) will be electromagnetically transferred from the primary to the secondary side, where they encounter a very high impedance of essentially an open circuit; the back-transformation of the very high impedance from the secondary side to the primary side significantly adds to the DC impedance of the primary coil, providing a combined high-value high-frequency impedance. Hence, the high frequency impedance of the SOTI can be orders of magnitude higher than the low-frequency impedance.

The SOTI can provide a low pass filter (for low frequencies (e.g., 0 Hz to 10 Hz), the impedance of the overall device can be significantly smaller than the overall impedance measured for higher frequency (e.g., hundreds of Hz and above) components). The frequency dependent impedance of the SOTI can be defined based on the frequency of the waveform, the electromagnetic coupling between the two or more coils of the SOTI, the DC impedance of the primary coil alone, and/or the high frequency impedance of the non-primary coil(s) (e.g., secondary, tertiary, etc.). The high frequency impedance of the non-primary coil can be changed from essentially an open circuit to smaller values by connecting one or more passive electric components (e.g., resistor, capacitor, inductor) to the non-primary coil. This can allow a higher frequency selectivity (e.g., the overall SOTI can provide a notch-filter characteristic instead of a low-pass filter characteristic).

As used herein, the term "neural prosthesis" or "neural prosthetic" can refer to one or more devices that can substitute for a neurological function (e.g., motor function, sensory function, cognitive function, etc.) that has been damaged (e.g., as a result of a neurological disorder). For example, a neural prosthesis can include a stimulation device that restores neurological function ("neural stimulation") and/or a blocking device that blocks nerve conduction ("nerve block"). The term "stimulation waveform," as used herein, can encompass an electrical waveform used for neural stimulation and an electrical waveform used for nerve block.

As used herein, the term "nerve" can refer to a "peripheral nerve." Generally, a peripheral nerve can refer to a nerve in a patient's body other than brain and spinal cord. A peripheral nerve can include a bundle of fibers (including motor and sensory fibers) that can connect the brain and spinal cord to the rest of the patient's body. For example, a peripheral nerve can control the functions of sensation, movement, and motor coordination. In some instances, the peripheral nerve can conduct information bi-directionally (e.g., providing both motor control and sensory feedback).

As used herein, the term "electric waveform" can refer to an electrical signal that can be generated by a waveform generator and applied to the nerve with an electrode to achieve neural stimulation or nerve block. In some instances, the electrical waveform can be a mathematical description of a change in voltage over time (or "voltage controlled") or a change in current over time (or "current controlled"). In some instances, the electric waveform can be a biphasic waveform. In other instances, the electric waveform can be a monophasic waveform. The terms "electric waveform," "stimulation waveform," and "signal" can be used interchangeably herein.

As used herein, the term "biphasic waveform" can refer to an electric waveform that includes both an anodic phase of the waveform and a cathodic phase. The anodic phase and the cathodic phase can be applied in either order. Examples of biphasic waveforms can include a pulsed waveform, a high frequency electric alternating current (KHFAC) waveform (e.g., in the kilohertz frequency range), a charge-balanced direct current (CBDC) waveform, or a multi-phased direct current (MPDC) waveform.

As used herein, the term "monophasic waveform" can refer to an electric waveform that includes a single phase of the waveform. The monophasic waveform can include a single anodic phase of cathodic phase.

As used herein, the term "waveform generator" can refer to a device that can generate the electric waveform that can be provided to an electrode. For example, the waveform generator can be connected to the electrode via one or more leads. In some instances, the waveform generator can be implanted within a patient's body. In other instances, the waveform generator can be external to the patient's body. The terms "waveform generator" and "stimulator" can be used interchangeably herein.

As used herein, the terms "direct current (DC) component," or "DC contamination" can refer to a constant frequency signal (e.g., zero Hertz noise) that contaminates the electrical waveform. Generally, application of the DC component to the nerve can present the risk of damaging the nerve and/or the electrode. In some instances, the waveform generator and/or wiring between the waveform generator and the electrode can contribute the DC component that contaminates the signal. In other instances, a DC-offset can contribute to the DC component.

As used herein, the term "noise" can refer to any component of a signal that is not the intended signal (e.g., the electrical waveform). In some instances, noise can be a component of the signal that contaminates or obscures the intended signal. Although noise can be irregular, it tends to have an average frequency. The average frequency can be a low frequency and/or high frequency. For example, low frequency noise can have a lower frequency than an electrical waveform used for neural stimulation and/or nerve block (e.g., DC contamination, zero Hertz noise). In another example, high frequency noise can have a higher frequency than the electrical waveform used for neural frequency and/or nerve block.

As used herein, the term "electrode" can refer to a device that provides an attachment for one or more contacts. The one or more contacts can be made of an interface material providing the conversion of current flow via electrons in a metal (wire/lead) to ionic means (in an electrolyte, such as interstitial fluid). In some instances, the electrode can aid in shaping the electric field generated by the contacts.

As used herein, the term "substantially eliminate" can refer to a complete (e.g., 100%) or partial (e.g., less than 100%, such as about 90%, about 80%, about 70%, about 60%, or less than about 50%) elimination of a DC-component from a electric waveform. The terms "substantially eliminate" and "eliminate" can be used interchangeably herein.

As used herein, the term "medical professional" can refer to can refer to any person involved in medical care of a patient including, but not limited to, physicians, medical students, nurse practitioners, nurses, and technicians.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to neural stimulation and nerve block and, more specifically, to systems and methods that can eliminate contaminating noise (e.g., low frequency noise and/or high frequency noise) from an electric waveform used for neural stimulation, nerve block, and/or neural sensing. For example, waveforms used for neural stimulation and nerve block can have DC contamination that can damage the nerve, even in the low micro Ampere (μA) range, especially when applied repeatedly and/or over long periods of time. The systems and methods of the present disclosure can filter the DC contamination from the waveform used for neural stimulation or nerve block so that the waveform used for neural stimulation or nerve block does not damage the nerve.

In some instances, commercially available and/or real-world waveform generators can add small DC-components to signals that include an electric waveform. When used over a prolonged time, the DC-components can lead to damage to the waveform generator, electrode destruction, or nerve damage. For example, the small DC-components can be the result of an imperfect balancing of the waveform generator's output stage. Even perfectly charge-balanced stimulation signals can lead to electrode destruction or nerve damage as side effects over longer stimulation times. Typically, in-line capacitors and/or shunting resistors can be used to filter the DC-components from the electric waveform. However, this approach is not feasible for continuously ongoing stimulation (e.g., high frequency alternating current with kilohertz frequency (KH-FAC) waveforms) since there is no inter-stimulation-interval that allows for shorting the accumulated charge within the in-line capacitors. If the shunting resistors are replaced by inductors placed in parallel with the stimulator and/or the electrode in combination with the in-line capacitors, the offset charge can be compensated for automatically, thereby protecting the waveform generator, the electrode, and the nerve tissue.

III. Systems

One aspect of the present disclosure can include a system that can remove contaminating noise (high frequency noise and/or low frequency noise) from an electric waveform. One application of the system is in neural stimulation and/or nerve block. Removing noise, such as DC contamination, from a stimulation signal can protect the nerve tissue from damage. Although neural stimulation and nerve block are described herein, it will be understood that noise can be removed from electric waveforms used for other applications.

Figure 1:
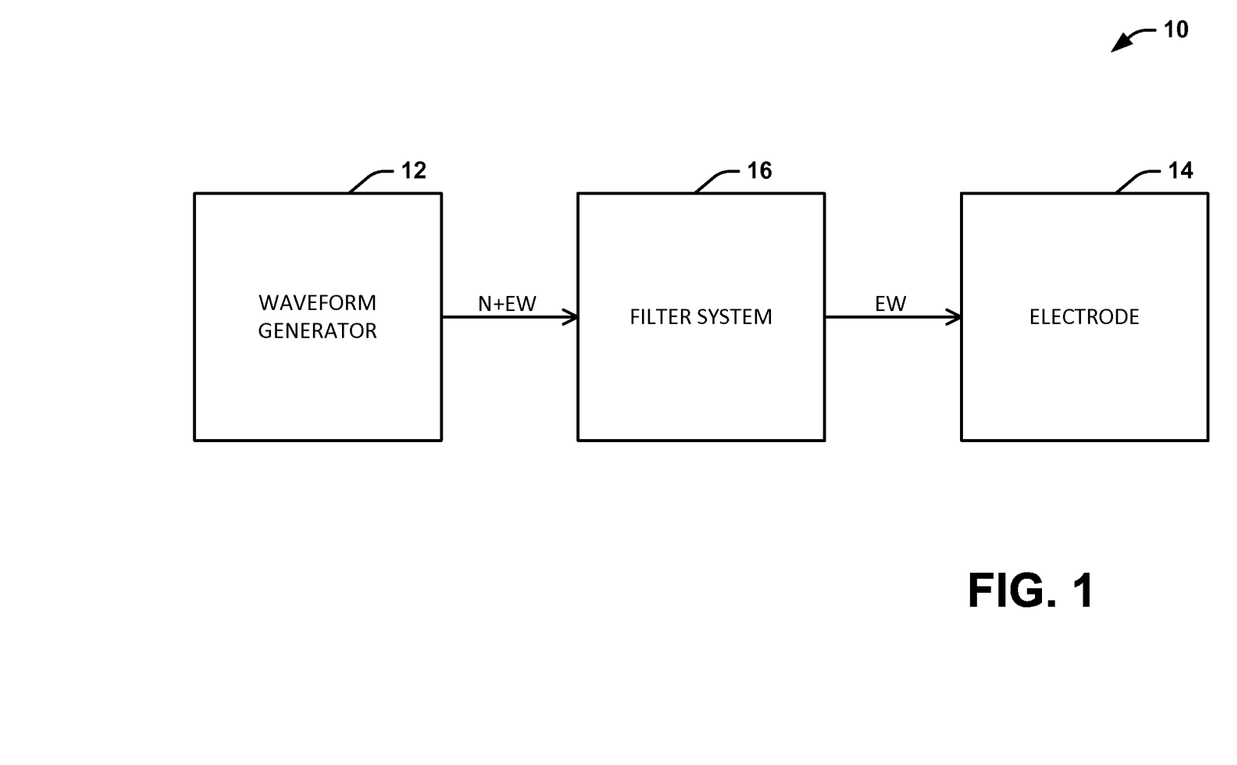
FIG. 1 is a schematic block diagram showing a system that can remove contaminating noise from an electric waveform in accordance with an aspect of the present disclosure.

FIG. 1 illustrates an example of a system 10 that can remove contaminating noise from a electric waveform, according to an aspect of the present disclosure. FIG. 1, as well as associated FIGS. 2-6, are schematically illustrated as block diagrams with the different blocks representing different components. One or more functions of one or more of the components (e.g., the waveform generator 12) can be implemented by computer program instructions. These computer program instructions can be provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the components specified in the block diagrams.

These computer program instructions can also be stored in a non-transitory computer-readable memory that can direct a computer or other programmable data processing apparatus to function in a particular manner, such that the instructions stored in the non-transitory computer-readable memory produce an article of manufacture including instructions, which implement the function specified in the block diagrams and associated description.

The computer program instructions can also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions of the components specified in the block diagrams and the associated description.

Accordingly, in some instances, the waveform generator 12 described herein can be embodied at least in part in hardware and/or in software (including firmware, resident software, micro-code, etc.). Furthermore, aspects of the waveform generator 12 can take the form of a computer program product on a computer-usable or computer-readable storage medium having computer-usable or computer-readable program code embodied in the medium for use by or in connection with an instruction execution system. A computer-usable or computer-readable medium can be any non-transitory medium that is not a transitory signal and can contain or store the program for use by or in connection with the instruction or execution of a system, apparatus, or device. The computer-usable or computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

In other instances, the waveform generator 12 does not require a memory and a processor. For example, the waveform generator 12 can be a body part (e.g., a muscle, a nerve, and/or an organ) that can generate an electrical signal (e.g., for a sensor).

As shown in FIG. 1, one aspect of the present disclosure can include a system 10 configured to remove noise from an electric waveform. The "noise" include noise with a lower frequency than the electrical signal (e.g., DC contamination) and/or noise with a higher frequency than the electrical signal. In some instances, system 10 can be embodied within a neural prosthesis device that can provide neural stimulation and/or nerve block to a nerve. For example, removing low frequency noise, such as DC contamination from a stimulation waveform used by the neural prostheses can protect the nerve from damage inherent to the DC contamination. Although neural stimulation and nerve block are described herein, it will be understood that the systems and methods described herein can be utilized with other applications that require an uncontaminated electrical signal.

The system 10 can include components including at least a waveform generator 12, an electrode 14, and a filter system 16. The waveform generator 12 can generate a signal (N+EW). The signal (N+EW) can include a electric waveform (EW) (intended) and noise (unintended). The electric waveform (EW) can be a voltage controlled waveform or a current controlled waveform. In some instances, the electric waveform (EW) can be a biphasic waveform. In other instances, the electric waveform (EW) can be a monophasic waveform. The noise (N) can contaminate the electrical signal. For example, the noise can be a DC-component (DC) that can be caused by a DC-offset inherent to the waveform generator 12, which can accumulate over time and contribute to the electric waveform no longer being perfectly charge-balanced. In some instances, if the DC-component were applied to the nerve repeatedly and/or over an extended period of time, the nerve could suffer irreversible damage. In other instances, the noise could damage the waveform generator 12 and/or the electrode 14. Moreover, if the signal (N+EW) is a monophasic waveform, system 10 can output a charge balanced biphasic waveform as the electric waveform (EW). In cases where the signal (N+EW) is already biphasic, the system 10 can balance the charge between the phases of the biphasic waveform to output a charge balanced biphasic waveform.

The electrode 14 can be configured to contact at least a portion of a nerve to apply the electric waveform (EW) to the nerve for neural stimulation or nerve block. The electrode 14 can be associated with one or more electrode contacts that can receive the electric waveform (EW) from the waveform generator 12. In some instances, the electrode 14 can be magnetically coupled to the electrode contact. In other instances, the electrode 14 can be capacitively coupled to the electrode contact. Examples of electrodes that can be used as electrode 14 include a nerve shaping electrode, an electrode array, a spiral electrode, a cuff electrode, a Huntington style electrode, a co-linear placed spinal cord stimulation (SCS) or deep brain stimulation (DBS) electrode, a disk electrode, an intra-muscular electrode, or an intra-fascicular electrode.

The filter system 16 can receive the signal (N+EW) from the waveform generator 12. The filter system 16 can be a passive system that eliminates the noise (N) from the electrical waveform (EW). For example, the filter system 16 can include one or more inductors and one or more capacitors. The filter system 16 can be located between the waveform generator 12 and the electrode 14. In some instances, the filter system 16 can be located between the contact and the electrode 14.

Upon receiving the signal (N+EW), the filter system 16 can filter the noise (N) from the electric waveform (EW) and provide the filtered electric waveform (EW) to the electrode 14.

In instances where the electric waveform (EW) is a monophasic waveform, the filter system 16 can output a charge balanced biphasic waveform. Accordingly, the waveform generator 12 need only generate the monophasic waveform and the filter system 16 can generate a charge balanced biphasic waveform to deliver to the electrode 14. This can reduce the power consumption associated with the generation of the waveform.

In instances where the electric waveform (EW) is a biphasic waveform, the filter system 16 can balance the charge within the biphasic waveform and output a balanced charge biphasic waveform. For instance, the filter system 16 can provide offset charge compensation to ensure that the biphasic waveform is charge balanced before delivery to the electrode 14. In some instances, the filter system 16 can include an LC-filter. The LC-filter can include at least one inductor and at least one capacitor. The at least one inductor can have an inductance chosen based on whether the filter system 16 is configured to filter low frequency noise (e.g., a DC component) or high frequency noise. In some instances, the inductance can be a frequency dependent inductance.

The filter system 16 can include a transformer (or "trafo-inductor"). For example, the transformer can be a secondary-side-open-transformer-inductor (SOTI). The SOTI can include a first coil and a second coil that are inductively coupled. The SOTI can provide a frequency dependent impedance that facilitates the removal of the noise from the electric waveform. A primary side of the SOTI can be configured to receive the electric waveform contaminated with the noise and output the electric waveform, and a secondary side of the SOTI can be configured to adjust the frequency-dependent impedance of the SOTI.

Figure 2:
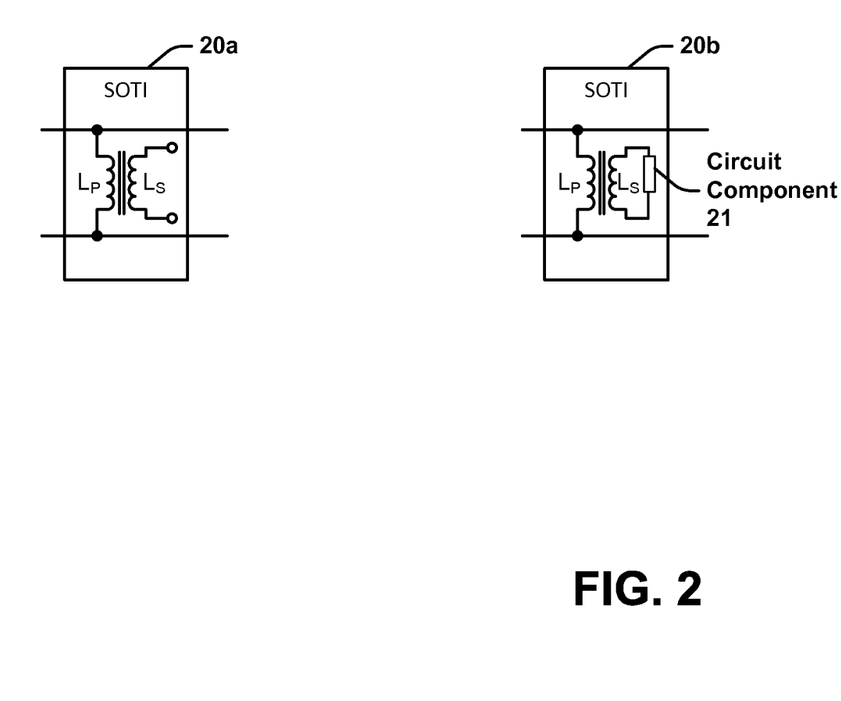
FIG. 2 includes schematic block diagrams showing two examples of a secondary-side-open-transformer-inductor (SOTI) that can be used within the filter system shown in FIG. 1.

FIG. 2 illustrates examples of possible SOTI devices. In one example, the SOTI 20a (representing a full SOTI) can include a primary winding (Lp) that provides a closed circuit with the waveform generator 12 and the electrode 14 and a secondary winding ($L_S$) that provides an open circuit. In another example, the SOTI 20b (representing a partial SOTI or more frequency-selective SOTI) can include a primary winding ($L_P$) that provides a closed circuit with the waveform generator 12 and the electrode 14 and a secondary winding ($L_S$) can form a closed circuit with a circuit component 21. For example, the circuit component 21 can include one or more active circuit components and/or passive circuit components (e.g., resistor, capacitor, inductor). In one example, the circuit component 21 can include a capacitor in series with a resistor (R) (e.g., the resistor can have a large resistance and the capacitor can have a small capacitance). In some instances SOTI 20b can reduce the impedance of SOTI 20a due to the circuit component 21. As an example, reducing the impedance can cause an overall notch filter characteristic for the electric waveform (EW).

In some instances, the filter system 16 can include the SOTI alone, more than one SOTI, and/or a passive component (resistor, inductor, capacitor). Example configurations 30-60 of the LC-filter that can be used by filter system 16 are shown in FIGS. 3-6, respectively. It will be appreciated that in FIGS. 3-6, each capacitor can be replaced by one or more additional or alternative passive component (e.g., resistor, inductor, capacitor). For example, either of the SOTIs 20a. 20b of FIG. 2 can be used as the SOTIs illustrated in FIGS. 3-6; however, other SOTI configurations may be used.

Figure 3:
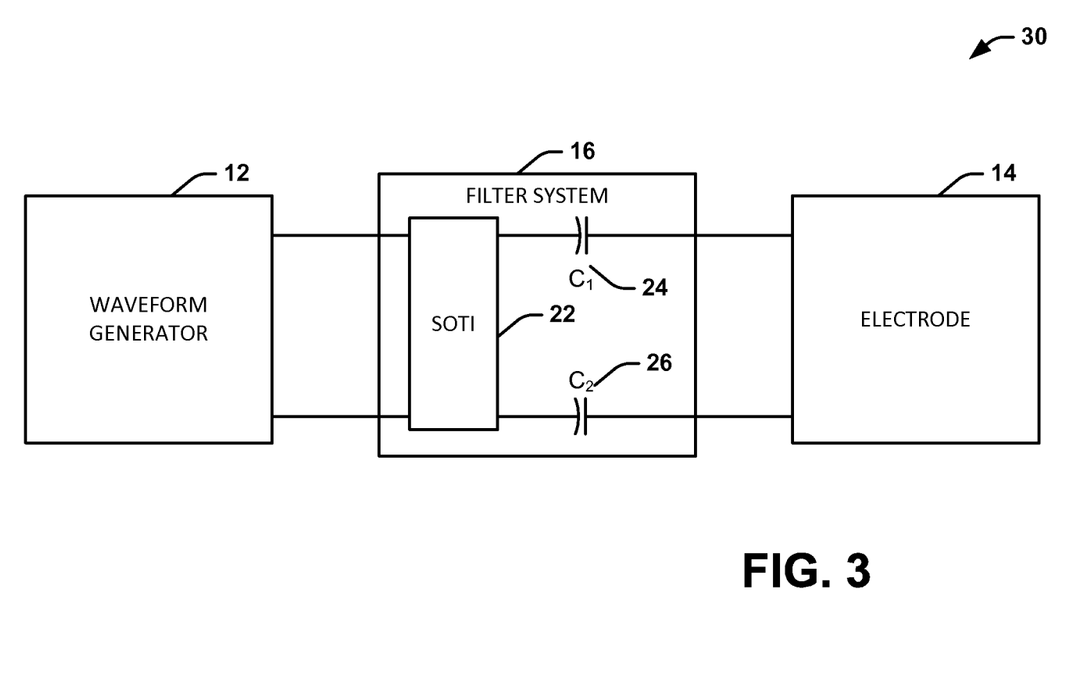
FIGS. 3-6 are schematic block diagrams showing additional example configurations of the filter system shown in FIG. 1.
Figure 4:
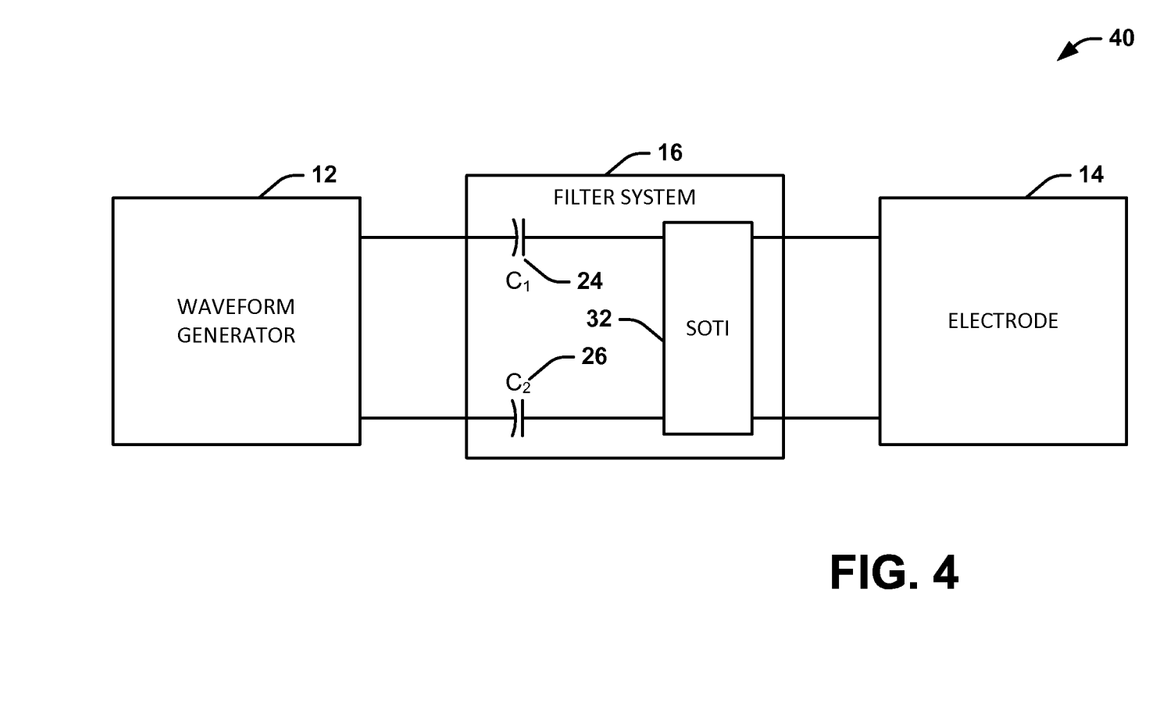
Figure 5:
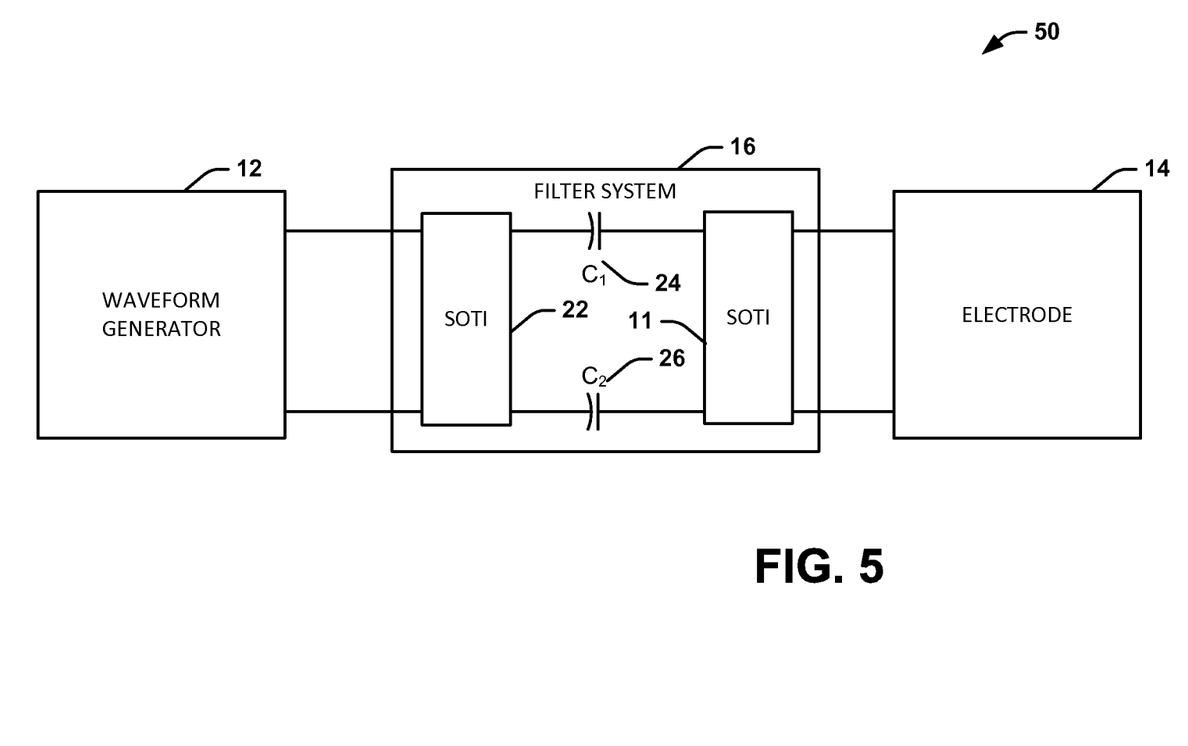

The configurations 30-50 shown in FIGS. 3-6 can be used to eliminate low frequency noise (e.g., a DC component) from the electrical signal. FIG. 3 illustrates an example 30 configuration of the filter system 16 with the SOTI 22 located in parallel to the waveform generator 12. FIG. 4 illustrates an example 40 configuration of the filter system 16 with the SOTI 24 located in parallel to the electrode 14. FIG. 5 illustrates an example 50 configuration of the filter system 16 with a first SOTI 22 located in parallel to the waveform generator 12 and a second SOTI 24 located in parallel to the electrode 14. Each example 30-50 includes two DC-blocking in-line capacitors ($C_1$, $C_2$). However, it will be understood that each of the configurations 40, 50, 60 could have just one or more than two passive components in the place of the illustrated DC-blocking in-line capacitors.

In the configurations 30-50, the capacitors ($C_1$, $C_2$) can provide a frequency-dependent impedance, with a high value impedance for low frequencies or DC waveform components and a low value impedance for high frequency waveform components. SOTI devices (e.g., SOTI 22, 24) can provide a frequency-dependent impedance (e.g., a low value impedance for low frequency or DC waveform components and a high value impedance for high frequency waveform components). For example, capacitors ($C_1$, $C_2$) can be used as high-pass filters and to de-couple electronics to biological tissue in applications for neural stimulation and block, as well as sensing electrical waveforms of neural and muscular origin. When used as filters, capacitors can provide a very high impedance to DC waveforms, as well as low-frequency waveforms.

For example, when used to de-couple a neural stimulator from an electrode that is in direct contact to biological tissue, capacitors located in at least one of the two (or more) electronic lines allow the passage of high-frequency (e.g., 5 kHz) components, while preventing the passage of low-frequency components (e.g., 0.1 Hz). The majority of the current passing through the capacitor does so as displacement current. The amount of displacement current that can pass through the capacitor is limited by (1) the capacitance of the capacitor and/or (2) the applied voltage across the capacitor (aka between the ends or connectors of the capacitor). Low-frequency waveforms, such as direct current (DC) waveforms that are applied across the capacitor can experience a large impedance as the voltage inside the capacitor increases, thereby opposing the applied voltage which originally caused the passage of currents through the capacitor. As the voltage inside the capacitor approaches the compliance voltage of the waveform generator 12 (or electric biological signal), signal information can be distorted during the passage through the capacitor and information can be either changed or lost. Accordingly, signals and waveforms (EW) that can be applied for neural stimulation or nerve, block as well as signals measured from neural or muscular origin can be in the frequency range from several hundred Hertz to hundreds of Kilohertz. These signals can pass the capacitive component, while any apparent low-frequency or DC voltage can be shorted through the inductive (SOTI) component.

In some instances, by combining a SOTI orthogonally with a capacitor, the high-pass filter characteristic of the capacitor can be enhanced by providing essentially a short circuit for the accumulating DC voltage across a capacitor that would be caused by low-frequency components in order to prevent the changing or loss of information that passes through the high-pass filter. Such a circuit can be accomplished, for example, by combining one capacitor and one SOTI, two capacitors and one SOTI, or two capacitors and two SOTI.

For example, when two capacitors and two SOTI are used with monophasic waveforms for neural stimulation or nerve block on the input side, then the output side automatically provides biphasic waveforms. These waveforms can be charge-balanced. If good quality capacitors and high-frequency-high-value SOTI are used, then the waveforms are likely to be almost fully charge-balanced.

If one or more SOTIs with bandpass characteristics (e.g., SOTI 20b) is used instead of a SOTI with low-pass characteristics, then partial charge balancing can be accomplished. In the case of monophasic waveforms on the input side, then the characteristics of the secondary, charge balancing, phase can be modified by the bandpass characteristic (e.g., pulse-width, amplitude, and/or shape) of the used SOTI.

Figure 6:
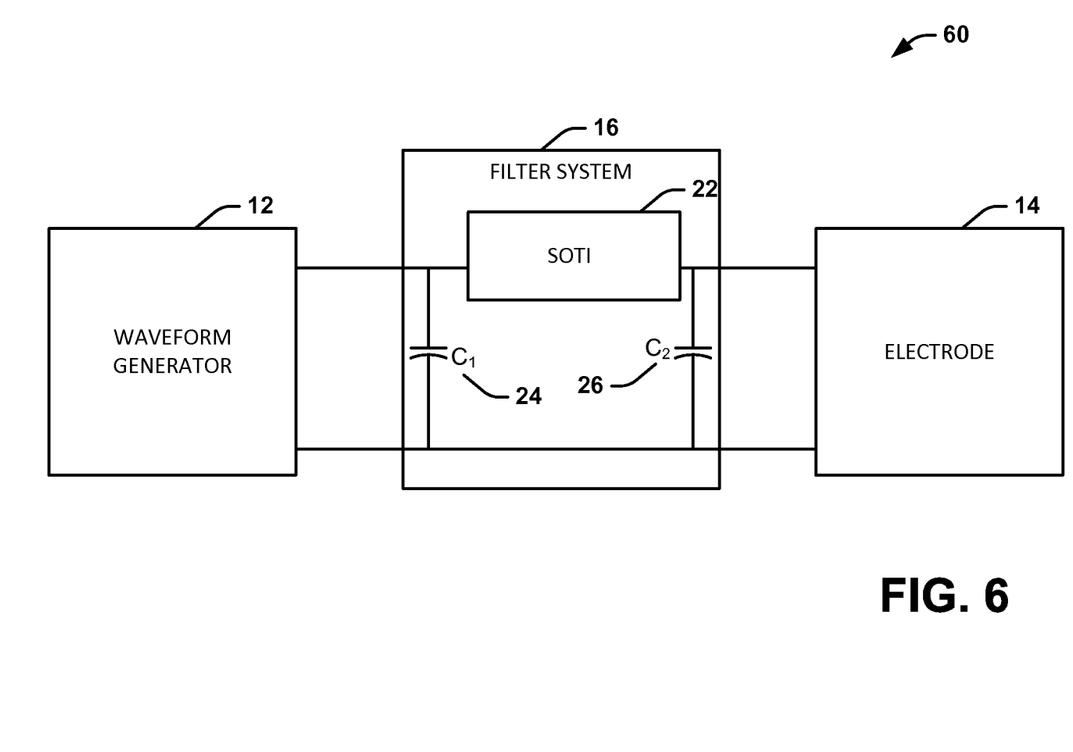

The example configuration 60 of the filter system 16 shown in FIG. 6 can be used to eliminate high frequency noise. The configuration 60 shows one SOTI 22, but it will be understood that configuration 60 can include more than one inductor in series with the waveform generator 12 and the electrode 14 (e.g., on either line). It will also be understood that example 60 can include just one or more passive components (resistors, inductors, capacitors).

By turning the components of the filter configurations of FIGS. 3-5 by 90 degrees, a low-pass filter for neural applications can be provided that can block unwanted high-frequency noise components (e.g., for DC nerve block) so that high frequency noise can be significantly reduced to improve the efficacy and reproducibility of the DC nerve block. For example, reducing high frequency noise can provide a ground signal during neural sensing and stimulation applications with reduced high frequency noise contamination.

IV. Methods

Another aspect of the present disclosure can include methods that can eliminate noise (e.g., low frequency noise and/or high frequency noise) from an electric waveform, according to an aspect of the present disclosure. For example, the electric waveform can be used for neural stimulation and/or nerve block. An example of a method 70 that can eliminate noise from a electric waveform is shown in FIG. 7.

Figure 7:
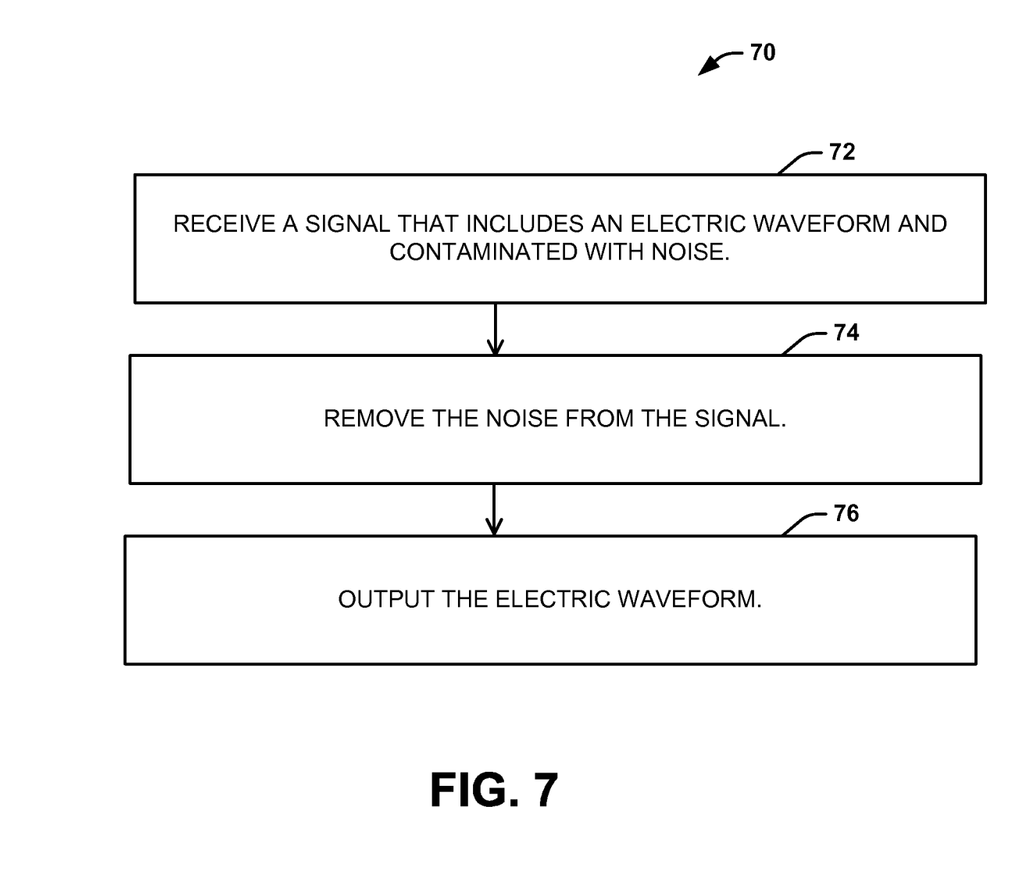
FIG. 7 is a process flow diagram illustrating a method for eliminating contaminating noise from an electric waveform in accordance with another aspect of the present disclosure.

The method 70 FIG. 7 is illustrated as process flow diagrams with flowchart illustrations. For purposes of simplicity, the method 70 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 70.

Referring to FIG. 7, an aspect of the present disclosure can include a method 70 for eliminating noise (e.g., low frequency or high frequency) from an electric waveform. The method 70 can be implemented by a passive filter system (e.g., passive filter system 30-60). In some instances, method 70 can be employed a neural prosthesis device that can provide neural stimulation and/or nerve block to a nerve. In some instances, the noise can be DC contamination. Removing the DC contamination from a stimulation waveform used by the neural prostheses can protect the nerve from damage inherent to the DC contamination.

At 72, a signal (e.g., N+EW) can be received (e.g., by a primary side of a SOTI 20a, 20b, 22, or 24)). The signal can include an intended electric waveform (e.g., EW) and corrupting noise (e.g., N) that is unintended. In some instances, the noise could cause damage to the waveform generator, the electrode, and/or the nerve.

The electric waveform can be a voltage controlled waveform or a current controlled waveform. In some instances, the electric waveform can be a biphasic waveform. In other instances, the electric waveform can be a monophasic waveform. Although the monophasic waveform can be damaging when applied to a nerve, the monophasic waveform provides the advantages of lower power consumption by the waveform generator. The SOTI can be configured to ensure that the input waveform is a charge-balanced biphasic waveform.

At 74, the noise can be removed from the signal (e.g., by the filter system 30-60). In instances where the electric waveform is a monophasic waveform, the filtering can involve creating a charge balanced biphasic waveform from the monophasic waveform. In instances where the electric waveform is a biphasic waveform, the filtering can involve ensuring that the biphasic waveform is charge balanced. For example, filtering the biphasic waveform can compensate for an offset charge compensation to provide the charge-balanced biphasic waveform.

At 76, the electric waveform (e.g., EW) without the noise can be output (e.g., by the SOTI or the filter system). In some instances, the electric waveform can be sent to the electrode for application to the nerve to facilitate neural stimulation or nerve block. The electric waveform can be applied to the nerve without damaging the nerve, the electrode, and/or the waveform generator.

From the above description, those skilled in the art will perceive improvements, changes and modifications. Such improvements, changes and modifications are within the skill of one in the art and are intended to be covered by the appended claims.

What is claimed is:

1. A system that removes noise from an electric waveform for neural stimulation or nerve block, the system comprising:
   a first coil of a secondary-side-open-transformer-inductor (SOTI) comprising one connector that represents an input and one connector that represents an output, wherein the input receives electric waveform contaminated with noise; and
   a second coil of the SOTI comprising two connectors that represent an electrically open circuit, wherein the second coil is inductively coupled to the first coil,
   wherein the second coil of the SOTI provides an impedance that facilitates removal of the noise from the electric waveform, and
   wherein the output of the first coil of the SOTI comprises the electric waveform without the noise.

2. The system of claim 1, further comprising a passive component connected to the first coil of the SOTI to modify a filter characteristic of the SOTI.

3. The system of claim 2, wherein the passive component comprises at least one of a resistor, an inductor, and a capacitor.

4. The system of claim 1, wherein the noise comprises a DC-component comprising a zero Hertz frequency.

5. The system of claim 1, wherein the noise comprises a frequency greater than a frequency of the electric waveform.

6. The system of claim 1, wherein the electric waveform is a monophasic waveform, and
   wherein the SOTI is configured to create a balanced charge-biphasic waveform from the monophasic waveform.

7. The system of claim 1, wherein the electric waveform is a biphasic waveform, and
   wherein the SOTI is configured to balance charge within the biphasic waveform.

8. A method for eliminating noise from an electric waveform for neural stimulation or nerve block by a passive filter system comprising a secondary-side-open-transformer-inductor (SOTI), the method comprising the steps of:
   receiving, by a connector of a first coil representing an input of the SOTI, the electric waveform contaminated with the noise;
   removing, by a second coil of the SOTI, the noise from the electric waveform; and
   outputting, by another connector of the first coil representing an output of the SOTI, the electric waveform,
   wherein the second coil is inductively coupled to the first coil, and
   wherein the second coil provides an impedance that facilitates the removal of the noise from the electric waveform by the filter system.

9. The method of claim 8, wherein the filter system further comprises a passive component electrically coupled to the first coil or the second coil of the SOTI,
   wherein the passive component comprises at least one of a resistor, an inductor, and a capacitor.

10. The method of claim 8, wherein the noise comprises a frequency less than the electric waveform.

11. The method of claim 10, wherein the noise comprises a DC component.

12. The method of claim 8, wherein the noise comprises a frequency greater than the electric waveform.

13. The method of claim 8, wherein the electric waveform is a biphasic waveform, and
   wherein the removing step further comprises balancing the charge within the phases of the biphasic waveform.

14. The method of claim 8, wherein the electric waveform is a monophasic waveform, and
   wherein the removing step further comprises creating a balanced charge-biphasic waveform from the monophasic waveform.

15. A device that removes contaminating noise from an electric signal for neural stimulation or nerve block, comprising:
   a passive filter system comprising a secondary-side-open-transformer-inductor (SOTI) and at least one passive component,
   wherein the SOTI comprises a first coil inductively coupled to a second coil,
   wherein the first coil comprises one connector that represents an input and one connector that represents an output, wherein the input receives electric waveform contaminated with noise,
   wherein the second coil comprises two connectors that represent an electrically open circuit, wherein the second coil is inductively coupled to the first coil,
   wherein the output of the first coil comprises the electric waveform without the noise, and
   wherein the second coil provides an impedance that facilitates removal of the contaminating noise from the electric waveform.

16. The device of claim 15, further comprising a second passive filter system comprising a second SOTI.

17. The device of claim 15, wherein the filter system is configured to balance charge within the electric waveform.

18. The device of claim 17, wherein the electric waveform contaminated with the noise is a monophasic waveform and the filter system is configured to balance charge within the electric waveform.

19. The device of claim 15, wherein the noise comprises a DC component.

* * * * *